US009504556B2

(12) United States Patent
Bebb et al.

(10) Patent No.: US 9,504,556 B2
(45) Date of Patent: Nov. 29, 2016

(54) FLEXIBLE STRETCH STENT-GRAFT

(75) Inventors: Debra A. Bebb, Chandler, AZ (US); Sandra M. Cundy, Mesa, AZ (US); Jürgen Dorn, Neulussheim (DE)

(73) Assignee: C. R. BARD, INC., Tempe, AZ (US)

( * ) Notice: Subject to any disclaimer, the term of this patent is extended or adjusted under 35 U.S.C. 154(b) by 949 days.

(21) Appl. No.: 13/023,371

(22) Filed: Feb. 8, 2011

(65) Prior Publication Data

US 2011/0166638 A1 Jul. 7, 2011

Related U.S. Application Data

(62) Division of application No. 12/280,954, filed as application No. PCT/EP2007/001729 on Feb. 28, 2007.

(60) Provisional application No. 60/776,918, filed on Feb. 28, 2006.

(51) Int. Cl.
*A61F 2/06* (2013.01)
*A61F 2/07* (2013.01)
(Continued)

(52) U.S. Cl.
CPC .. *A61F 2/07* (2013.01); *A61F 2/89* (2013.01); *A61F 2/915* (2013.01); *A61F 2002/072* (2013.01); *A61F 2002/075* (2013.01); *A61F 2002/828* (2013.01)

(58) Field of Classification Search
CPC ............ A61F 2/07; A61F 2/89; A61F 2/915; A61F 2002/072; A61F 2002/075; A61F 2002/828
USPC ..................... 623/1.13, 1.44, 1.12
See application file for complete search history.

(56) References Cited

U.S. PATENT DOCUMENTS

| 454,082 A | 6/1891 | Stephenson |
| 3,953,566 A | 4/1976 | Gore |

(Continued)

FOREIGN PATENT DOCUMENTS

| EP | 1164972 A1 | 1/2002 |
| WO | 9800090 A2 | 1/1998 |

(Continued)

OTHER PUBLICATIONS

PCT/EP2007/001729 filed Feb. 28, 2007 Preliminary Report on Patentability dated Sep. 2, 2008.

(Continued)

*Primary Examiner* — Julie A Szpira
(74) *Attorney, Agent, or Firm* — C. R. Bard Intellectual Property; Buchalter Nemer

(57) ABSTRACT

A stent device includes a first graft member, a second graft member and a stent frame defining a central axis. The frame has an abluminal surface engaged with the first graft member and a luminal surface engaged with the second graft member such that the first graft member and the second graft member encapsulates the stent frame along the length of the central axis. The stent frame includes a configuration where the stent frame is disposed on a curvature such that the abluminal surface has a radius of curvature of approximately 20 millimeters about a center of the curvature and the luminal surface defines a substantially constant effective cross-sectional area at any portion generally transverse to the central axis of the stent frame disposed about the curvature.

12 Claims, 11 Drawing Sheets

(51) Int. Cl.
*A61F 2/82* (2013.01)
*A61F 2/89* (2013.01)
*A61F 2/915* (2013.01)

(56) References Cited

U.S. PATENT DOCUMENTS

| | | |
|---|---|---|
| 4,187,390 A | 2/1980 | Gore |
| 4,482,516 A | 11/1984 | Bowman et al. |
| 4,545,082 A | 10/1985 | Hood |
| 5,282,847 A | 2/1994 | Trescony et al. |
| 5,476,506 A | 12/1995 | Lunn |
| 5,507,767 A | 4/1996 | Maeda et al. |
| 5,653,745 A | 8/1997 | Trescony et al. |
| 5,713,917 A | 2/1998 | Leonhardt et al. |
| 5,749,880 A * | 5/1998 | Banas et al. ............. 606/198 |
| 5,800,456 A | 9/1998 | Maeda et al. |
| 5,824,037 A | 10/1998 | Fogarty et al. |
| 5,824,042 A | 10/1998 | Lombardi et al. |
| 5,899,935 A | 5/1999 | Ding |
| 5,928,279 A | 7/1999 | Shannon et al. |
| 6,004,348 A * | 12/1999 | Banas et al. ............. 623/23.7 |
| 6,010,530 A | 1/2000 | Goicoechea |
| 6,013,854 A | 1/2000 | Moriuchi |
| 6,039,755 A | 3/2000 | Edwin et al. |
| 6,059,808 A | 5/2000 | Boussignac et al. |
| 6,110,198 A | 8/2000 | Fogarty et al. |
| 6,123,722 A | 9/2000 | Fogarty et al. |
| 6,124,523 A | 9/2000 | Banas et al. |
| 6,139,573 A | 10/2000 | Sogard et al. |
| 6,193,745 B1 | 2/2001 | Fogarty et al. |
| 6,214,039 B1 | 4/2001 | Banas et al. |
| 6,238,409 B1 | 5/2001 | Hojeibane |
| 6,264,684 B1 | 7/2001 | Banas et al. |
| 6,267,834 B1 | 7/2001 | Shannon et al. |
| 6,331,191 B1 * | 12/2001 | Chobotov ............. 623/1.44 |
| 6,344,052 B1 | 2/2002 | Greenan et al. |
| 6,352,554 B2 | 3/2002 | De Paulis et al. |
| 6,451,047 B2 | 9/2002 | McCrea et al. |
| 6,551,351 B2 | 4/2003 | Smith et al. |
| 6,558,414 B2 | 5/2003 | Layne |
| 6,579,314 B1 * | 6/2003 | Lombardi et al. ........... 623/1.44 |
| 6,626,938 B1 | 9/2003 | Butaric et al. |
| 6,656,219 B1 | 12/2003 | Wiktor |
| 6,673,103 B1 | 1/2004 | Golds et al. |
| 6,773,457 B2 | 8/2004 | Ivancev et al. |
| 6,786,920 B2 | 9/2004 | Shannon et al. |
| 6,790,225 B1 | 9/2004 | Shannon et al. |
| 6,790,226 B2 * | 9/2004 | Edwin et al. ............. 623/1.13 |
| 6,797,217 B2 | 9/2004 | McCrea et al. |
| 6,923,828 B1 | 8/2005 | Wiktor |
| 6,974,471 B2 * | 12/2005 | Van Schie et al. .......... 623/1.12 |
| 7,285,132 B2 * | 10/2007 | Tseng et al. ............. 623/1.46 |
| 7,318,835 B2 * | 1/2008 | Berra ............. 623/1.12 |
| 7,550,003 B2 * | 6/2009 | Sogard et al. ............. 623/1.13 |
| 7,597,775 B2 | 10/2009 | Sogard et al. |
| 2003/0017775 A1 | 1/2003 | Sowinski et al. |
| 2003/0088305 A1 | 5/2003 | Van Schie et al. |
| 2003/0139797 A1 * | 7/2003 | Johnson et al. ............. 623/1.13 |
| 2003/0225447 A1 | 12/2003 | Majercak et al. |
| 2004/0019375 A1 | 1/2004 | Casey et al. |
| 2004/0034408 A1 | 2/2004 | Majercak et al. |
| 2004/0049264 A1 | 3/2004 | Sowinski et al. |
| 2004/0098092 A1 | 5/2004 | Butaric et al. |
| 2004/0181278 A1 * | 9/2004 | Tseng et al. ............. 623/1.46 |
| 2004/0236402 A1 | 11/2004 | Layne et al. |
| 2004/0236415 A1 | 11/2004 | Thomas |
| 2005/0070994 A1 | 3/2005 | Sievers et al. |
| 2005/0096998 A1 | 5/2005 | Gieselmann et al. |
| 2006/0030926 A1 * | 2/2006 | Berra ............. 623/1.13 |
| 2006/0058867 A1 * | 3/2006 | Thistle et al. ............. 623/1.13 |
| 2006/0155359 A1 | 7/2006 | Watson |
| 2007/0198079 A1 | 8/2007 | Casey et al. |
| 2007/0208409 A1 | 9/2007 | Quigley |
| 2007/0219622 A1 | 9/2007 | Kuppurathanam |
| 2007/0250146 A1 | 10/2007 | Cully et al. |

FOREIGN PATENT DOCUMENTS

| | | |
|---|---|---|
| WO | 0045742 A1 | 8/2000 |
| WO | 03034948 A | 5/2003 |
| WO | 2006020222 A | 2/2006 |

OTHER PUBLICATIONS

PCT/EP2007/001729 filed Feb. 28, 2007 Search Report dated May 7, 2007.
PCT/EP2007/001729 filed Feb. 28, 2007 Written Opinion dated Aug. 31, 2008.
U.S. Appl. No. 12/280,954, filed Aug. 27, 2008 Non-Final Office Action dated Nov. 26, 2010.

* cited by examiner

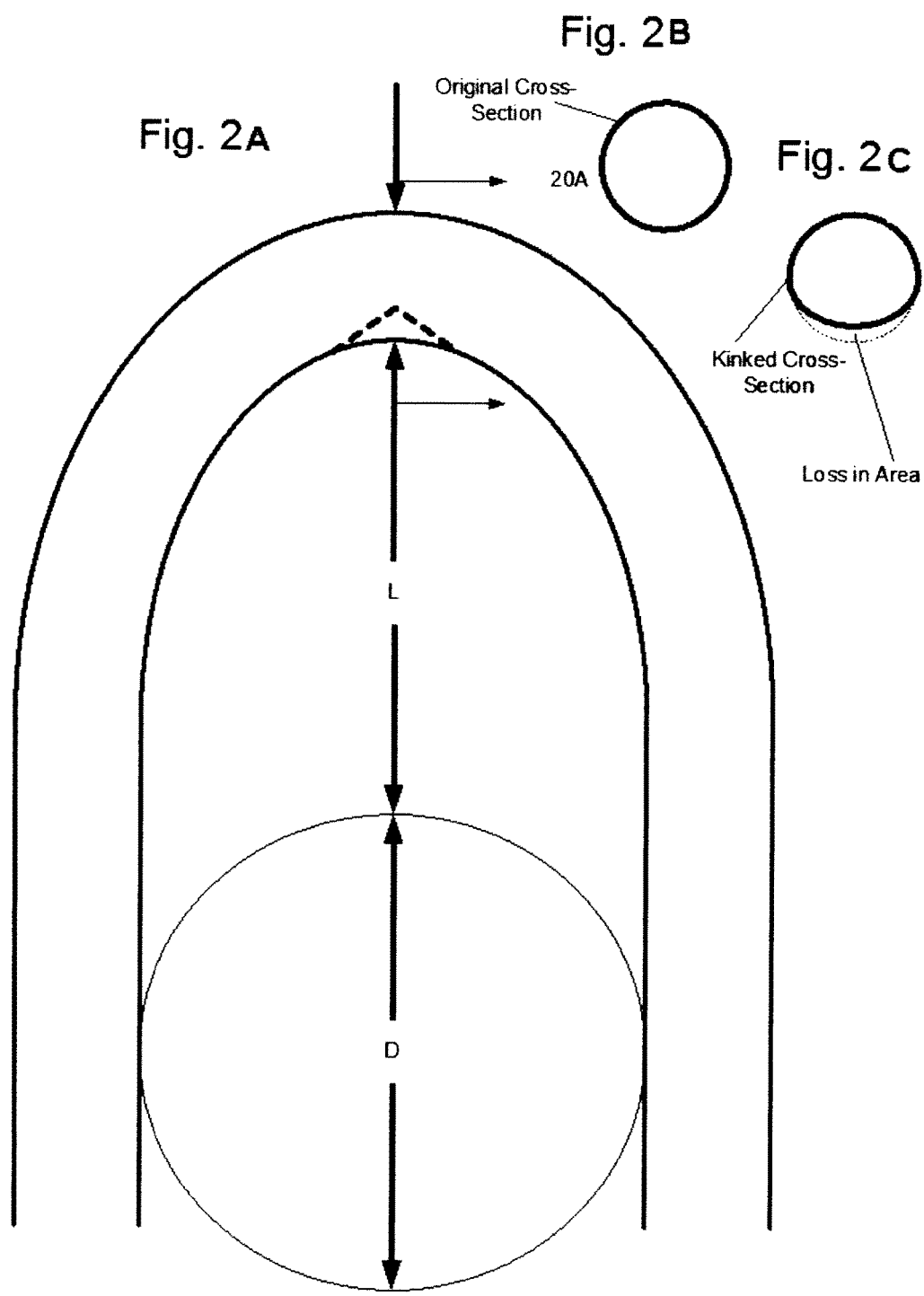

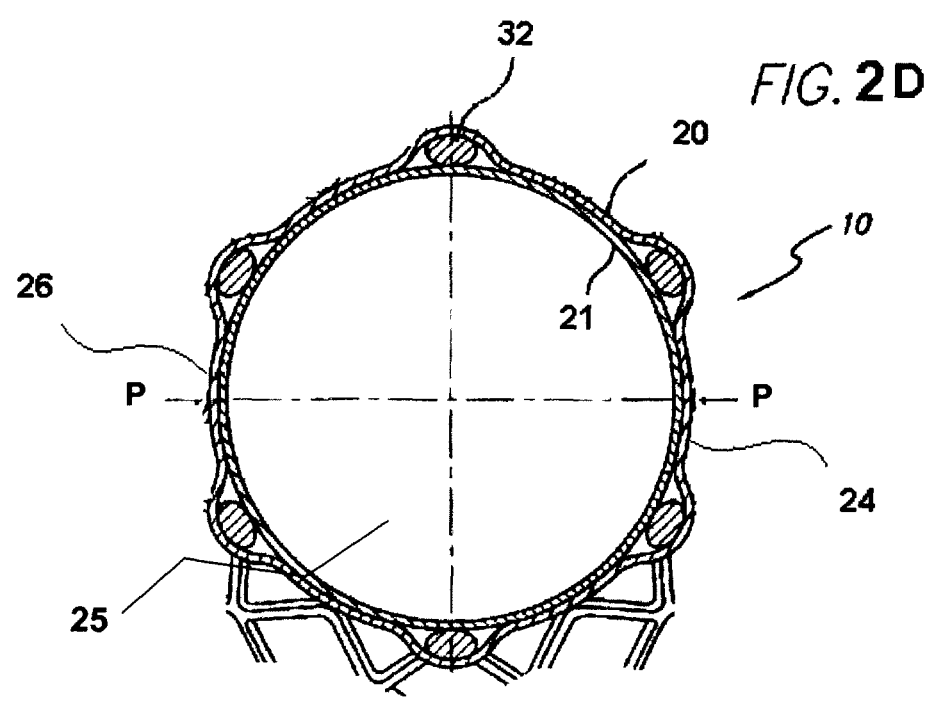

FLEXIBLE STRETCH STENT-GRAFT

PRIORITY

This application is a division of U.S. patent application Ser. No. 12/280,954, filed as a U.S. national stage application under 35 USC §371 of International Patent Application No. PCT/EP2007/001729, filed Feb. 28, 2007, claiming priority to U.S. Provisional Patent Application No. 60/776,918, filed Feb. 28, 2006, each of which is incorporated by reference into this application as if fully set forth herein.

BACKGROUND OF THE INVENTION

The present invention relates generally to the field of medical devices, and more particularly, to the stent grafts and their method of making.

Stents and similar endoluminal devices are currently used by medical practitioners to treat tubular body vessels or ducts that become so narrowed (stenosed) that flow of blood or other biological fluids is restricted. Such narrowing (stenosis) occurs, for example, as a result of the disease process known as arteriosclerosis. While stents are most often used to "prop open" blood vessels, they can also be used to reinforce collapsed or narrowed tubular structures in the respiratory system, the reproductive system, bile or liver ducts or any other tubular body structure. However, stents are generally mesh-like so that endothelial and other tissues can grow through the openings resulting in restenosis of the vessel.

Apart from use of stents within the circulatory system, stents have proven to be useful in dealing with various types of liver disease in which the main bile duct becomes scarred or otherwise blocked by neoplastic growths, etc. Such blockage prevents or retards flow of bile into the intestine and can result in serious liver damage. Because the liver is responsible for removing toxins from the blood stream, is the primary site for the breakdown of circulating blood cells and is also the source of vital blood clotting factors, blockage of the bile duct can lead to fatal complications. A popular type of stent for use in the biliary duct has been one formed from a shape memory alloy (e.g., nitinol) partially because such stents can be reduced to a very low profile and remain flexible for insertion through the sharp bend of the bile duct while being, self-expandable and capable of exerting a constant radial force to the duct wall.

Polytetrafluoroethylene (PTFE) has proven unusually advantageous as a material from which to fabricate blood vessel grafts or prostheses, tubular structures that can be used to replace damaged or diseased vessels. This is partially because PTFE is extremely biocompatible causing little or no immunogenic reaction when placed within the human body. This is also because in its preferred form, expanded PTFE (ePTFE), the material is light and porous and is readily colonized by living cells so that it becomes a permanent part of the body. The process of making ePTFE of vascular graft grade is well known to one of ordinary skill in the art. Suffice it to say that the critical step in this process is the expansion of PTFE into ePTFE. This expansion represents a controlled longitudinal stretching in which the PTFE is stretched to several hundred percent of its original length.

Cellular infiltration through stents can be prevented by enclosing the stents with ePTFE. Early attempts to produce a stent covered by ePTFE focused around use of adhesives or physical attachment such as suturing. However, such methods are far from ideal and suturing, in particular, is very labor intensive. More recently methods have been developed for encapsulating a stent between two tubular ePTFE members whereby the ePTFE of one-member touches and bonds with the ePTFE of the other member through the mesh opening in the stent. However, such a monolithically encapsulated stent may tend to be rather inflexible. Moreover, even covered stents that include slit cut and bridge connection designed graft coverings tend to be inflexible because the covering graft material is unable to expand lengthwise with the underlying stent frame.

Other solutions to provide a more flexible stent graft include a stent graft device described in U.S. Pat. No. 6,579,314 which is incorporated herein in its entirety by reference thereto. U.S. Pat. No. 6,579,314 describes a flexible stent graft that uses a partially encapsulated stent having areas covered by only a single layer of ePTFE in order to provide flexibility to the stent graft device. Another partially encapsulated stent is shown and described in U.S. Pat. No. 6,558,414 which is also incorporated herein in its entirety by reference thereto.

Other solutions provide for making a self-expanding stent longitudinally expandable. For example, U.S. Pat. No. 5,899,935 includes a method of manufacturing a stent in which the stent is stretched longitudinally to reduce its outer diameter and coated in a material to freeze the stretched configuration. In the description of use, the coating is disintegrated to permit the stent to expand.

SUMMARY OF THE INVENTION

In one preferred embodiment of a stent graft, the stent graft is configured to prevent cellular infiltration and maintain its flexibility to ensure ease of insertion and deployment of the stent graft by providing the ability to accommodate extreme anatomical curves. The stent graft device preferably includes a first graft member, a second graft member and a stent frame defining a central axis. The frame has an abluminal surface engaged with the first graft member and a luminal surface engaged with the second graft member such that the first graft member and the second graft member encapsulate the stent frame along the length of the central axis. The stent frame further preferably includes a configuration where the stent frame is disposed about a center of curvature such that the abluminal surface has a radius of curvature of approximately 20 millimeters from the center of curvature and the luminal surface defines a substantially constant effective cross-sectional area at any portion generally transverse to the central axis of the stent frame. Moreover, the stent frame further preferably includes a substantially straight portion continuous with the curvature which defines an effective cross-sectional area substantially equal to an effective cross-sectional area proximate the curvature.

In another aspect of the preferred stent graft device, the curvature of the stent frame includes a gap proximate the apex of the curvature, the gap having a gap length, the first graft member having an expansion portion configured to span the gap, the expansion portion defining a radius of curvature substantially equal to about 20 millimeters. The radius of curvature can further range from about 30 millimeters to about 10 millimeters.

In another preferred embodiment, the stent device includes a stent frame having a central axis, a luminal surface, and an abluminal surface. The stent frame has at least one gap along the abluminal surface providing communication between the abluminal and luminal surfaces and further defining a gap length. A generally tubular graft member is contiguous with at least one of the luminal and abluminal surfaces of the stent frame. The graft member preferably includes an expansion portion to span the at least one gap. The expansion portion has a length greater than the gap length and which is preferably defined by the stent frame having a radius of curvature of about 20 mm.

In yet another embodiment, the stent device includes a stent frame having a first end and a second end defining a central axis therebetween. A tubular graft member is preferably concentrically bound with the stent frame, and the graft member includes at least one undulation between the first and second ends, the tubular graft member being configured to extend along the central axis. Preferably, the stent frame has first and second states, wherein in the first state the stent frame is substantially straight such that the at least one undulation is disposed proximate a gap in the stent frame and in the second state the stent frame defines a radius of curvature expanding the gap so as to eliminate the undulation.

According to a preferred method of making a stent-graft device, the method, at least, can be achieved by tensioning a stent frame having an abluminal surface and a luminal surface to alter an initial aspect ratio of the stent frame and define a second aspect ratio. In addition, the preferred method further includes coupling a tubular graft member to the stent frame, and relaxing the stent frame so as to contract the graft member along the central axis. The method may include positioning the tubular graft member coaxially inside the stent and may include coupling the tubular graft member to the abluminal surface. The method further preferably includes disposing the first tubular graft member over a mandrel and securing a first and second end of the first tubular graft member about the mandrel. Tensioning the stent frame provides axially elongating the frame such that the frame is preferably elongated by about fifteen to twenty percent (15%-20%) of its original length. Relaxing the stent frame contracts the stent graft device to a length that is preferably about one hundred ten percent to about one hundred fifteen percent (110%-115%) of the original stent frame length. More preferably, relaxing the stent frame provides the stent graft device with an expansion length that is about five to ten percent (5%-7%) the contracted length of the stent graft device.

BRIEF DESCRIPTION OF THE DRAWINGS

The accompanying drawings, which are incorporated herein and constitute part of this specification, illustrate exemplary embodiments of the invention, and together, with the general description given above and the detailed description given below, serve to explain the features of the invention. It should be understood that the preferred embodiments are not the invention but are some examples of the invention as provided by the appended claims.

FIGS. 2A-2C schematically illustrate a test protocol for kinking.

FIG. 2D is a cross-sectional view of the device of FIG. 2 through the line IID-IID.

DETAILED DESCRIPTION

Figure 1:
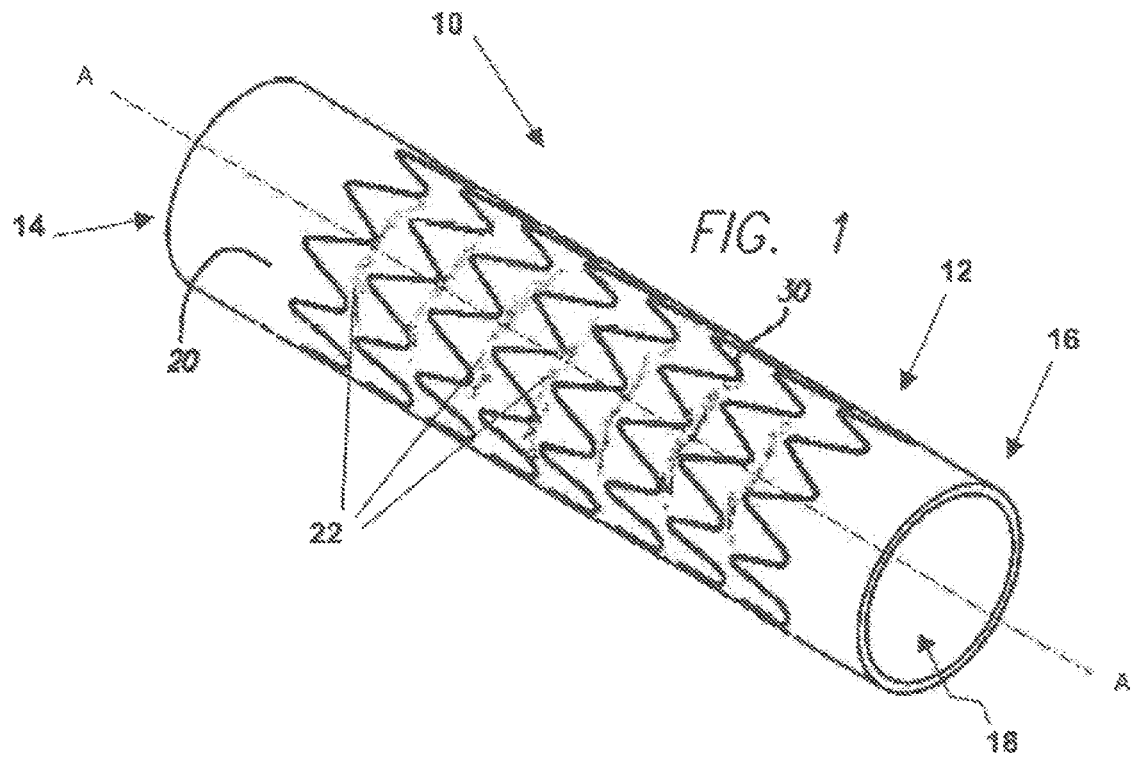
FIG. 1 illustrates a preferred stent graft device.
Figure 2:
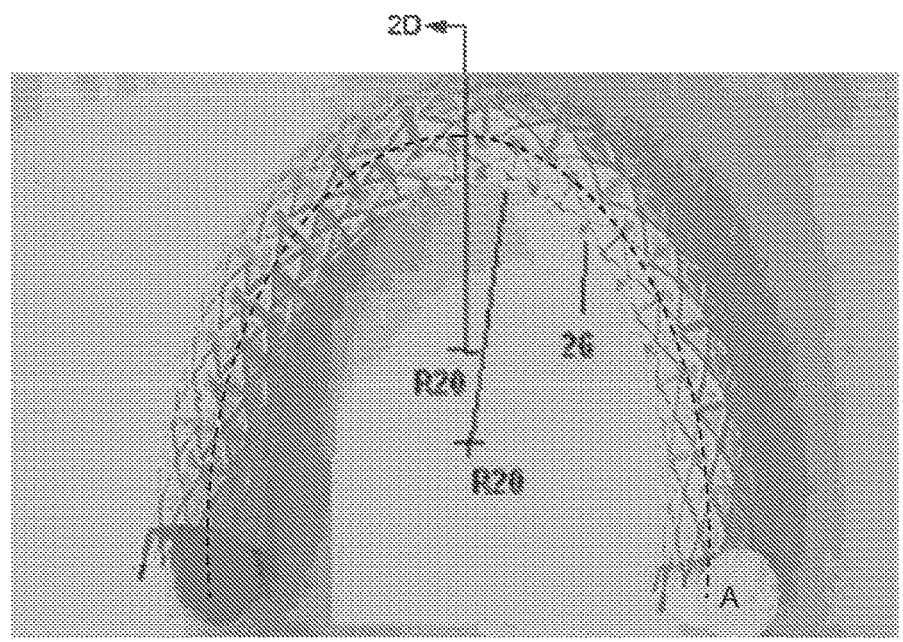
FIG. 2. illustrates the device of FIG. 1 in a bent configuration.

A preferred stent graft device 10, as illustrated in FIG. 1 includes a substantially tubular and elongated body 12 having opposing first and second ends 14, 16 spaced apart along a central axis A-A encapsulated in a sleeve of graft material 20. The body 12 includes a central passageway or interior chamber 18 dimensioned and configured for the passage therethrough of biological fluids such as, for example, blood. The tubular body 12 and the interior passageway 18 are preferably circular cylindrical although other cross-sectional geometries are possible, such as rectangular, oval, multi-lobed or polygonal, provided the body includes the interior passageway 18 sufficiently dimensioned for carrying the blood or other biological fluid. The tubular body 12 is preferably configured to articulate flex and/or bend in order to, for example, follow anatomical curves encountered during deployment and implantation. In a curved configuration, the tubular body 12 of defines a radius of curvature R from a center of curvature off the tubular body, as illustrated in FIG. 2, to define an outer curved surface 24 and an inner curved surface 26. The radius of curvature R for the body 12 can range from an infinite radius or a substantially straight configuration down to a radius of about 20 millimeters which corresponds substantially to the most severe anatomical curvature likely to be encountered or traversed in a body. The radius curvature at about 20 millimeters, in the most severe anatomical curvature configuration for the body 12, can more specifically range from about 30 millimeters to about 10 millimeters.

More preferably, the tubular body 12 can articulate, flex and/or bend about the radius of curvature R of about 20 millimeters with a high kink resistance. As noted above, the interior passageway 18 defines a chamber through which biological fluids pass, preferably at a desired flow rate. Accordingly, the interior passageway 18 of the stent graft device 10 defines an effective cross-sectional area through which such biological fluids can pass. The effective cross-sectional area is preferably at its maximum when the stent graft device 10 is in a substantially straight configuration. "Kink resistance" is preferably defined as maintaining a substantially constant effective cross-sectional area for the stent graft device 10 over the range of possible curvatures as the stent graft device 10 is bent from a substantially straight configuration to a bent configuration having a radius of curvature as small as about 20 millimeters. "Kink resistance" of a graft can be determined by utilization of the following protocol, as illustrated in FIGS. 2A, 2B and 2C.

In this protocol, the stent graft device 10 with high kink resistance is curved about a generally circular pin having a predetermined diameter D. The stent graft device 10 tangentially contacts the pin at two diametrically opposed portions on the test pin so that the stent graft device 10 defines two parallel substantially straight portions having a curve therebetween with an apex coincident with the outer surface of the stent graft device at a distance L from the closest surface of the pin to the apex, where L is approximately the same as D (FIG. 2A). A stent graft device 10 that does not kink, as discussed above, maintains an effective cross-sectional area proximate the apex that is essentially the same as the effective cross-sectional area for the substantially straight portions of the stent graft device 10 (FIG. 2A). More preferably, the effective cross-sectional area remains constant along the entire length of the stent graft device 10. Therefore, kinking can therefore be defined as the change in cross-sectional area proximate the apex of a curved portion as compared to a substantially straight portion of the device (FIG. 2B).

Kinking can be further defined as the point at which there is a threshold change in the effective cross-sectional area shown, for example, in FIG. 2C. More specifically, kinking results in a loss of cross-sectional area proximate the apex of the curved portion so as to define a cross-sectional area that is less than about 50 percent of a cross-sectional area in a substantially straight portion of the stent graft device, and is more preferably about 66% of the cross-sectional area in the substantially straight portion for a given diameter of the test pin. It should be noted that the cross-sectional area can be determined in a circular cross-section graft by calculating the inside diameter using the formula for circular area (radius squared times the constant pi). However, for ease of calculations, the outside diameter of the graft can be used instead.

An alternative method can be used to determine the presence of kinking or alternatively the absence thereof in a device using unaided visual cues. For example, to determine whether a stent graft device 10 is kink resistant, the device can be deployed in a test tube (not shown) having a radius of curvature of 20 millimeters to observe the behavior of the device with regard to the ability to appose the wall of the tube. When observed with an unaided eye, the absence of kinking is apparent by visual cues such as, for example, the absence of protrusions of struts to the vessel lumen.

Moreover, for the tubular body 12 to articulate, flex and/or bend without substantially kinking, it is to be understood that along the central axis A-A in the region the apex of the bend or curvature, the outer and inner curved surfaces 24, 26 defined by the encapsulation sleeve 20 remain substantially equidistant from the central axis A-A, as illustrated in FIG. 2. Because, the outer sleeve 20 does not kink or twist in response to the bend of the device 10, as discussed above, the interior dimensions and/or effective cross-sectional area of the tubular body 12 can remain substantially constant over the length of the device so as not to disturb the flow of biological fluids therethrough. More preferably, when the stent-graft device is in the bent configuration in the absence of kinking, the interior 18 of the tubular body 12 continues to define a substantially circular cross-sectional area along the length of the stent-graft device 10.

The outer sleeve 20 is further preferably bonded or coupled to an inner sleeve 21 or inner tubular member of graft material to form a monolithic encapsulation of a stent frame 30. The inner sleeve 21 lines the interior chamber 18 of the tubular body 12 to provide a smooth surface over which biological fluids can flow. To facilitate the capability of the device 10 to articulate, bend and/or flex without kinking, the sleeve 20 preferably includes a microfold, expansion portion or fold 22 that permits the sleeve to elongate and contract in the longitudinal direction in response to the articulation, bending and/or flexing of the tubular body 12. The device 10 can include multiple expansion folds 22 spaced along and radially disposed about the central axis A-A to provide flexibility to the body 12 bent to a radius of curvature. In the region of the curvature, and more preferably proximate the apex of the curvature, the expansion folds 22 along the central axis A-A preferably expand along the outer curved surface 24 and contract along the inner curved surface 26 in response to the bend of the tubular body 12.

The elongation of the expansion fold 22 and contraction of the expansion fold 22 along the inner surface 26 permits the outer surface 24 and the inner surface 26 to maintain a substantially constant parallel distance relative to one another over the entire length of the device 10, and thus maintain a substantially constant effective cross-sectional area over the length of device 10 for a range of radii of curvatures including a radius of about 20 millimeters. Accordingly, the sleeve 20 does not show any characteristics that would be considered kinking or twisting over the length of the device 10 in response to a severe bend configuration in the body 12. Therefore for example, where the interior chamber 18 of the stent graft device 10, in a substantially straight configuration, defines the effective cross-sectional area for the device 10 through which biological fluids flow, in the bent configuration, the expansion folds 22 maintain the outer curved surface 24 and the inner curved surface 26 equidistant from the central axis A-A such that the effective cross-sectional area is maintained. Shown in FIG. 2D is an illustrative effective area 25 of the stent graft 10 at the apex of the curvature in which the effective area 25 is symmetric about a plane P bisecting the length of the stent graft device 10.

Figure 3:
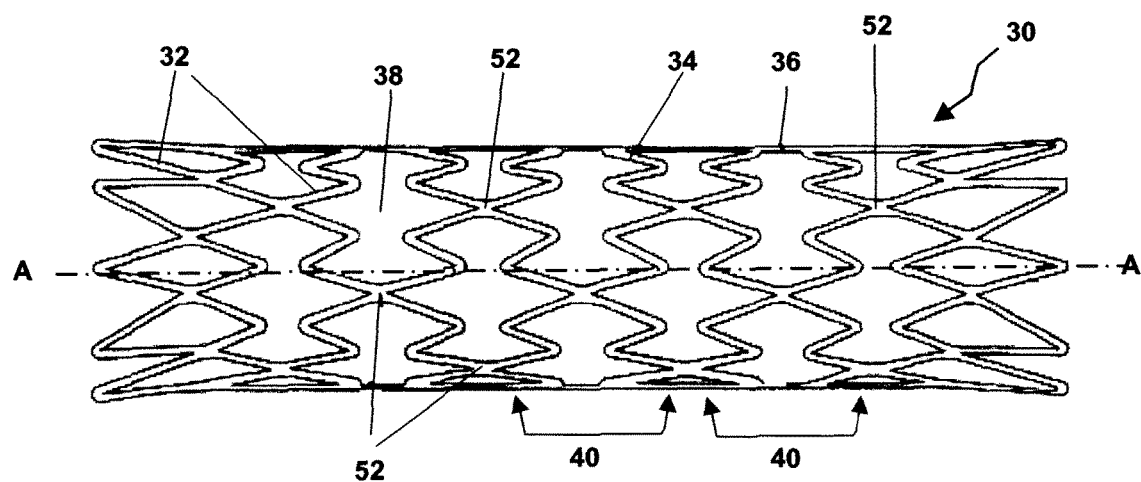
FIG. 3 is an illustrative embodiment of a stent frame for use in the preferred stent graft device.

The tubular body 12 of the stent graft device 10 includes an encapsulated stent frame 30, for example as shown in FIG. 3 in a bare or unencapsulated state. The stent frame 30 of the device 10 provides the structural rigidity to the stent graft device 10 and also preferably provides the device 10 with its flexibility. The stent frame 30 is preferably constructed of a shape memory alloy. Alternatively, the stent frame 30 can be made out of any type of material besides shape memory alloy so long as the frame 30 is constructed to bend and flex. Preferably, a plurality of interconnected struts 32 form the stent frame 30 including an abluminal surface 34 and a luminal surface 36 of the stent frame 30. The abluminal surface 34 defines the outer surface of the device 10 and the luminal surface 36 defines the interior passageway 18. Preferably, the stent frame is substantially circular cylindrical and the luminal surface 36 defines a substantially circular cross-sectional area. The plurality of interconnected struts 32 preferably intersect and connect at joints 52 disposed along and radially about the central axis A-A. The struts 32 further preferably interconnect to form a rhombus or other polygon having an interstice or gap 38 which provide communication between the abluminal surface 34 and the luminal surface 36. The struts 32 of the stent frame 30 are preferably interconnected such that the struts 32 can move relative to one another thereby permitting the stent frame to articulate, bend and/or flex.

Although the expansion folds 22 provide flexibility to the stent graft device 10, the stent frame 30 can be of any geometry configured to further enhance the flexibility of the device 10. Accordingly, various stent frame designs can be employed. For example, stent frame 30 can be formed as a single unitary piece, or alternatively, the stent frame is preferably constructed from the plurality of zigzag ring stents 40 (stenting zones), as seen in FIG. 3, joined at joining points 52 along central axis A-A. Preferably, there is a joining point 52 between a given ring stent 40 and an adjacent ring stent 40 every third strut 32 with the joining points 52 alternating from the left-hand adjacent to the right hand adjacent ring stent 40 so that six struts 32 separate the joining points 52 between any two ring stents 40. Gaps 38 are framed by the struts 32 and the joining points 52 where the intersections of zigzag struts are not joined. More preferably, each ring stent 40 is attached to each adjacent ring stent 40 by only a pair of joining points 52.

A stent frame 30 as described above is substantially similar to the stent frame of the LUMINEXX, billiary stent, from Bard Peripheral Vascular, Inc (hereinafter "Bard"). Alternatively, the stent frame 30 can be configured as stent frames used in other known stent graft devices such as, for example, Memotherm Flexx stents or Flexx stents also by Bard. A preferred design for stent frame 30 includes a plurality of interconnected circumferential zones, ring stents 40, struts or joints, as shown herein, to form the stent frame with gaps or interstices between the struts. However, it will be appreciated by those familiar in the art, that the stent frame 30 can have alternative configurations.

The stent frame 30 can, for example, be formed from wire, flat wire, or ribbon that is processed and shaped to form a stent frame 30 for use in the stent graft device 10. More specifically, the stent frame can be formed from a single wire that is bent to form sinusoidal waves or other periodic undulations. The wire can then be helically would about a cylindrical center to form the stent frame 30. In another helical arrangement, one or more wires can be weaved into a helical pattern to form the tubular stent frame 30 in which adjacent helical turns of the wire form parallel struts capable of flexible axial movement relative to one another. Alternatively, a stent frame 30 can be formed from the interconnection of ring stents 40 that are each formed from an axial flat ribbon of wire. To form an individual ring stent 40, the flat ribbon of wire can undergo a material removal process so as to form a series of parallel and staggered slits. The ribbon can be elongated and its transverse ends can be connected to form a ring stent 40 having an undulating wave pattern upon radial expansion.

The material removal process can be implemented such that the wave pattern has varying amplitudes along its length. The waves form the struts of the individual ring stent 40. Two or more of the ring stents 40 can be interconnected by one or more strut connectors disposed around the periphery of the stent rings 40 to form the substantially tubular stent frame 30. The connectors can be disposed at an angle relative to the central axis to provide tangential intersection of parallel struts between two adjacent ring stents 40. The tangential intersection of parallel struts can accommodate flexing of the stent within paired struts without interference between adjacent stent segments. In addition, the ring stents 40 can be disposed on and interconnected relative to one another such that the parallel planes defined by the cross-sectional areas of each ring stent 40 each define a common angle relative to the central axis of the stent frame 30. More preferably, the stent frame 30 is formed from a single tube of material that can undergo a material removal process to form the substantially tubular stent frame 30. Material can be removed from the tubular member so as to form a series of parallel struts or undulations that are capable of movement relative to one another to permit expansion of the stent frame 30. The material removal process can form undulating sign waves of constant or varying amplitude; alternatively, the material process can form helical turns along the axial length of the tubular member.

For example, a spiral stent frame 30 can be formed from a single tubular member in which spiral, helical or other continuous voids are cut into the tubular member to form the stent frame having interstices along its length. Generally, the material removal process can form any pattern in the tubular member that provides for adjacent struts that can move relative to one another to permit expansion and flexing in the stent frame 30. Exemplary alternative configurations of the stent frame 30 that can be used in stent graft device 10, including those described herein, are shown and further described in the following patent documents: U.S. Pat. No. 5,899,935.; U.S. Pat. No. 6,551,351; U.S. Pat. No. 6,656,219; U.S. Pat. No. 6,923,828; U.S. Pat. No. 5,507,767; U.S. Pat. No. 5,800,456; U.S. Pat. No. 6,059,808; U.S. Pat. No. 6,013,854; U.S. Pat. No. 6,010,530; and U.S. Pat. No. 6,238,409.

Figure 4A:
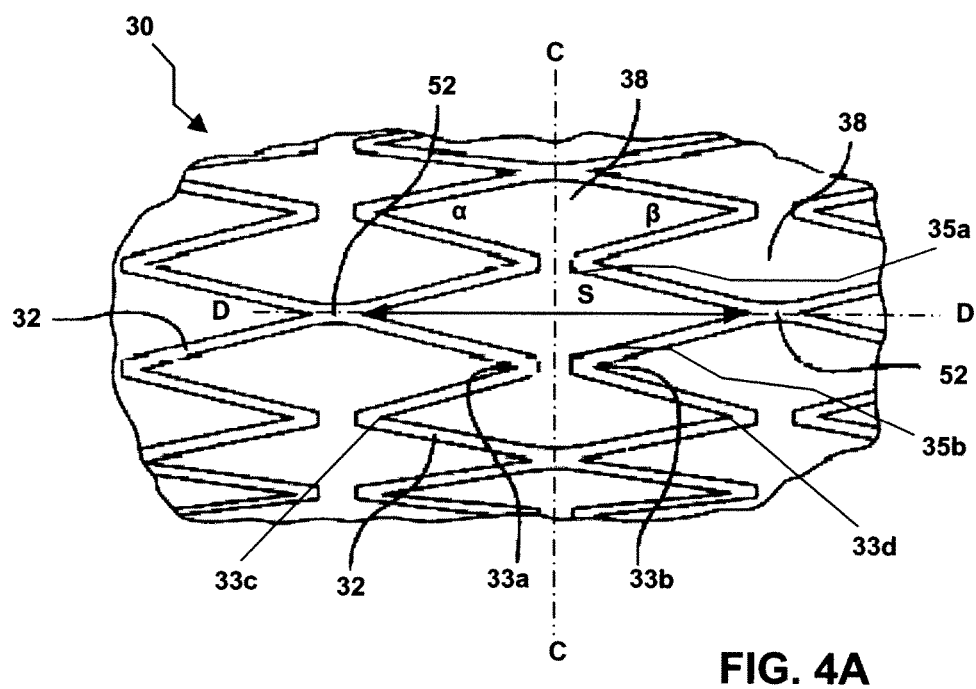
FIG. 4A is a detail of a schematic view of the stent frame in the device of FIG. 2.

Again referring to the stent frame 30 of FIG. 3, the interstices or gaps 38 between the joining points 52 permit the struts 32 to move relative to one another thereby making the stent frame 30 flexible for articulation or bending. The gap 38 defines an initial gap length when no load is placed on the stent device 10, i.e. when the stent device 10 is neither under tension nor compression. A stent ring 40 in the no load state, as seen for example in FIG. 4A, defines the gap 38 having an axial gap length s. The axial gap length s can be measured between any two points of the stent region or ring 40 that are opposite one another about an imaginary central axis C-C. For example, the axial gap length can be measured between points 33a and 33b located at the two inner most apexes of the stent ring 40, but alternatively and preferably, the axial gap length is measured between the outer most apexes of the stent ring 40, at points 33c, 33d. Preferably, the initial axial gap length s in a stent ring 40 in a no load state is preferably about 0.15 millimeters, but the axial gap length s can range from as much as about 3 to about 6 millimeters, preferably between about 3 and 5 millimeters and can be about 3.7 millimeters. A gap height of gap 38 can be defined by two points such as, for example, points 35a, 35b of the stent region or ring 40 that are opposite one another about the an imaginary axis D-D parallel to the central axis A-A. In addition, the zig-zag struts 32 can define one or more initial included angles, angle α and angle β which vary with the contraction and elongation of the stent frame as it moves between a substantially straight configuration to a substantially bent configuration. The included angles α, β can further quantify or define a characteristic configuration of the stent ring 40 and gap 38. Accordingly, because various stent frames can be employed, the struts 32 and stent ring points 33a, 33b, 35a, 35b defining the gap lengths, gap heights and included angles may vary and can be measured from various reference points and/or angles.

Figure 4B:
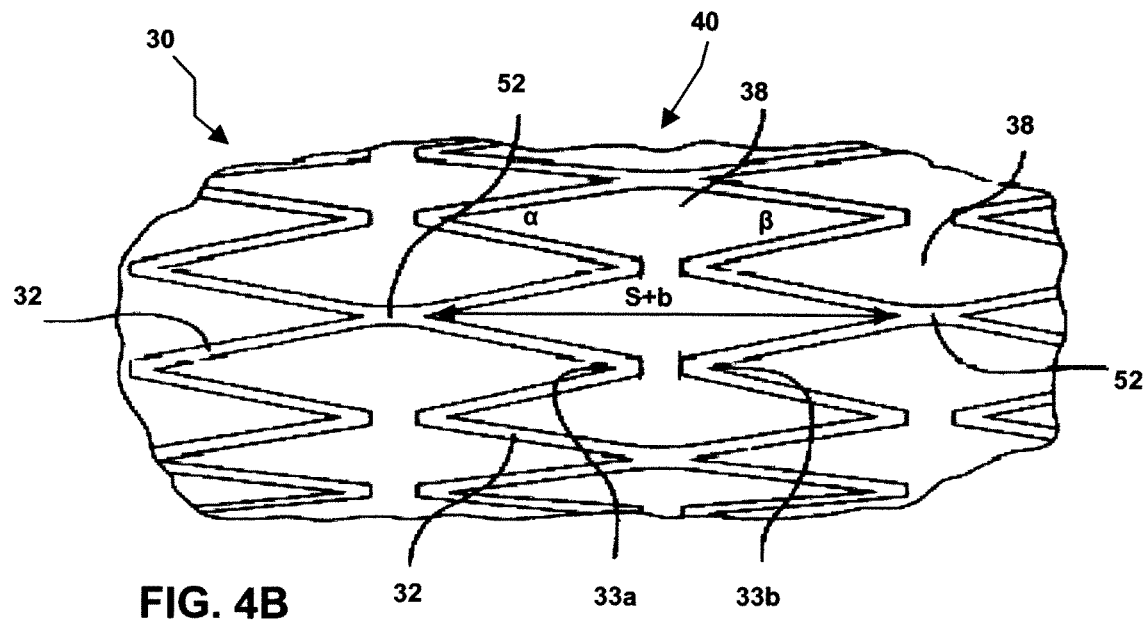
FIG. 4B is another detail of the of the stent frame in the device of FIG. 2.

When the stent graft device 10 is bent in a curved configuration. The outer curved surface 24 and the inner curved surface 26, relative to the center of curvature, are respectively in tension and compression. Accordingly, the portion of the stent ring 40 located on the outer curved surface 24 is under tension, and conversely the portion of the stent ring 40 located along the inner surface 26 is under compression. When the stent ring 40 is under compression, the axial gap length is less than when the gap is under no load or in tension. When the stent ring 40 is under tension, as shown in FIG. 4B, the axial gap length s widens along the axis of elongation by a change in length of an amount b so as to define a total axial gap length s+b. The increase in the gap length b is equal to about five to twenty percent of the gap length in the no load condition, preferably is about five to about ten percent, and more preferably about seven percent of the gap length in the no load state. Preferably, the axial gap length s+b is at its maximum when the stent ring 40 is located at the outer curved surface 24 at the apex of a radius of curvature of about 20 millimeters, i.e. a preferred minimum stent radius. The increased axial gap length when the stent is in tension can range from about 0.15 millimeters to about 0.5 millimeters depending upon the original gap length.

Figure 5A:
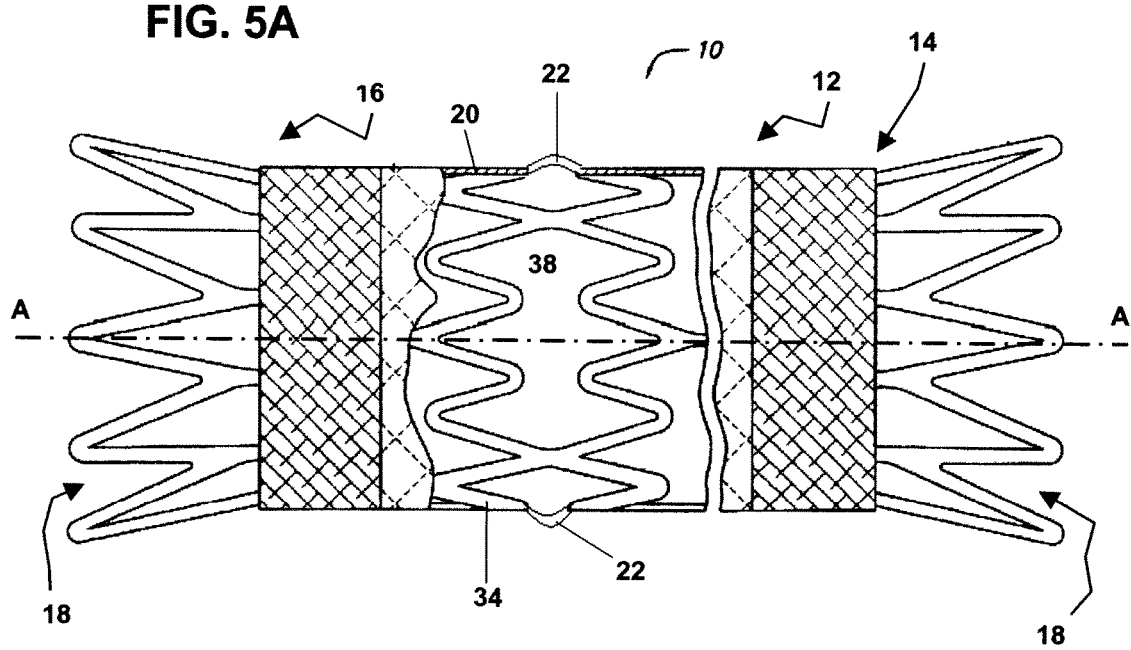
FIG. 5A is a cross-sectional view of another preferred stent graft device.

A lengthwise cross-sectional view of an illustrative embodiment of the stent graft device 10 is shown in FIG. 5A. The encapsulation sleeve 20 of the stent device 10 preferably includes one or more microfolds, expansion portions or folds 22 spanning at least one gap 38 of the stent frame 10. The expansion folds 22 provide kink resistance to the stent graft device 10 by enabling the axial expansion and contraction of the sleeve 20 in response to the relative movement of the struts 32. In addition, the expansion folds 22 of the graft material along the outer surface of the stent graft device 10 can define one or more longitudinally extending undulations along the length of the stent graft device 10.

An undulation can be a portion of the expansion fold 22 formed by the graft material spanning the gap 38 of the stent frame 30 so as to have at least one of a peak and a valley. Preferably, the undulations are configured and disposed uniformly along the length of the device 10 so as to evenly distribute the graft material. The even distribution of the graft material can minimize the profile of the stent graft device 10 by preventing areas of concentration of graft material along the outer surface. A preferred undulation can be formed where the length of the expansion fold 22 is about 5-20 percent longer than the gap length of the gap 38, preferably about 5-10 percent longer and more preferably about 7 percent longer than the length of gap 38. With the stent graft device 10 in the bent configuration, the outer curved surface 24 preferably does not include an undulation as the length of the expansion portion 22 is about equal to the arc formed by the axial length of the gap 38. Accordingly, the undulations can appear and disappear from the profile of the stent graft device 10, as the device 10 articulates and/or flexes through a range of curvatures.

The minimized profile of the stent graft device, when in the straight configuration, can further minimize the resistance experienced when loading the device 10 into a stent delivery device such as a catheter or sheath. Preferably, the minimized profile permits the stent graft to be loaded into reduced size sheath. For example, where known stent graft having a diameter of 10 millimeters and a length of 100 millimeters, i.e. a 10/100 stent graft device was loaded into a 9 French (F) sheath, a stent device configured according to the preferred embodiment produces a profile capable of being loaded into an 8 F sheath. Moreover, the presence of the expansion folds 22 in the stent device 10 allows the device 10 to be loaded into a sheath with minimized force as the expansion folds 22 permit contraction of the device 10 thereby minimizing the resistive force to loading. More specifically, the expansion folds absorbs the loading force that would normally add to the axial stress in the stent frame. In addition, the expansion folds 22 act as a beading on the stent graft device 10 by reducing the line contact with the sheath.

The expansion fold 22, being configured to expand and contract axially with the expansion and contraction of the stent frame 30, provides the flexibility of the device 10. Thus, where the gap 38 widens along the central axis in response to the bending of the stent frame 30, the expansion portion 22 unfolds or elongates in the same direction by a corresponding arc length. In addition, where a gap 38 of the stent frame 30 contracts in response to the same bend, the covering expansion portion 22 contracts accordingly. Because the encapsulation sleeve 20 can expand and contract with the stent frame 30 via the expansion portions 22, the outer sleeve can articulate, bend and/or flex with a high kink resistance.

Figure 5B:
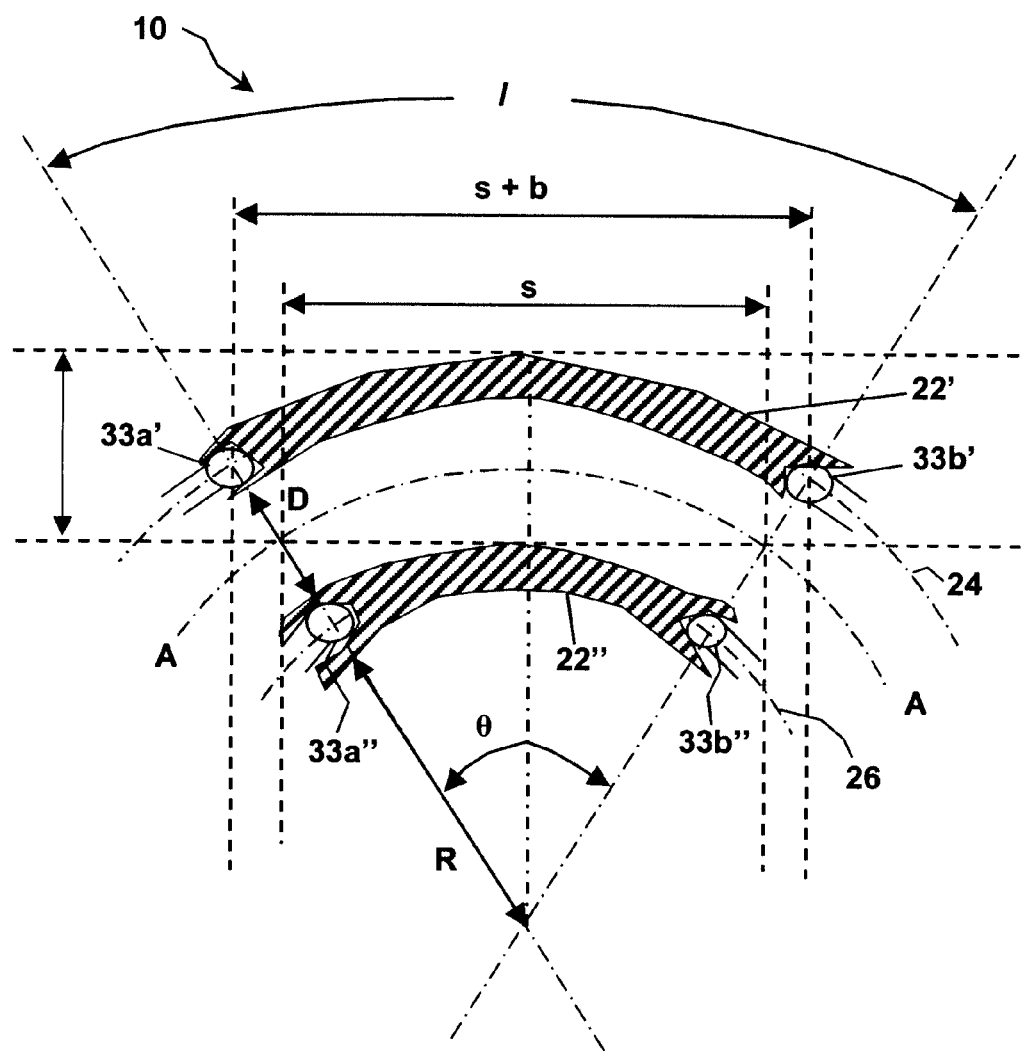
FIG. 5B is a detailed cross-section view of another preferred stent graft device.

Again referring to FIG. 5B, shown is an illustrative embodiment of the stent graft device 10 in a bent configuration such that the outer sleeve 20 defines a radius of curvature, preferably of about 20 millimeters. More specifically, shown is an expansion fold 22 having expansion portions 22', 22" respectively on the outer and inner curved surfaces 24, 26 of the stent device 10 in corresponding expanded and contracted states. The absence of kinking in any stent graft device 10 necessarily provides that the graft material on the inner curved surface 26 axially contracts by a length equal to the outer amount by which the graft material on the outer curved surface 24 axially lengthens.

In the bent configuration, the points 33a', 33b' further define a chord of a circle having a radius equal to the radius of curvature for the bent configuration. The chord is substantially equal to the expanded gap length between 33a' and 33b', for example, s+b. In one embodiment, the arc length l defining the minimum length of the expansion portion 22' is about equal to the expanded gap length s+b and therefore, as described above, is substantially equal to about 105-120 percent of gap length s, preferably about 105-110 percent of gap length s, and more preferably about 107 percent of gap length s. In the bent configuration, the points 33a', 33b' of the frame 38 further defines an angle θ which can be approximately solved for from the relation:

$$\sin(\theta/2) \approx (s+b)/(R+D)$$

Preferably, the expansion portions 22', 22" have an axial length at least as long as arc length defined by a the maximum length of the gap 38. For example, the expansion portion 22' has an axial length l, preferably substantially equal to the arc length defined by opposing points of a stent region or ring 40, i.e., points 33a', 33b' at their maximum axial gap length such as where, for example, the stent device 10 is in a bent configuration having a radius of curvature of about 20 millimeters. Conversely, the points 33a", 33b" along the inner curved surface 26 are in a maximum contracted configuration. Preferably, the radius of curvature is measured from the outer curved surface 24 although the radius of curvature could be measured from another reference line, for example, from the central axis A-A or the inner curved surface 26. With the stent device in its severe curvature configuration, the expansion portion 22' along the outer curved surface 24 is preferably longitudinally expanded such that the expansion portion 22' was substantially parallel to the central axis A-A over the length of the expansion portion 22. More preferably, the expansion portion 22" along the inner curved surface is contracted so as to form at least one undulation over the length of the curvature.

In order that the expansion portions 22', 22" expand and contract to the proper length so as to avoid kinking, and therefore maintain the effective cross-sectional area of the stent graft device 10, the expansion portions 22', 22" must have an appropriate axial length relative to the length of the gap 38 in the stent frame 30. A preferred method of forming the stent-graft device 10 and its expansion portions 22 generally provides elongating the stent frame 30 from an initial aspect ratio to define a second aspect ratio before encapsulating the stent frame 30 in graft material. Accordingly, the method of formation further provides affixing a tubular graft member to or concentrically about the stent frame 30 in its elongated state, and relaxing the assembly such that the stent frame 30 returns or contracts to define a third aspect ratio, the third aspect ratio generally being in the range between the first and the second aspect ratio.

The aspect ratio of a stent frame 30 can be defined as the ratio of the stent frame length to the stent frame diameter. The aspect ratio of an unloaded stent frame, i.e. under neither tension nor compression, can vary. For example, the aspect ratio (length to diameter ratio) determined in millimeters of an unloaded stent frame can be: 40:5; 120:5; 120:7; 120:8; 120:9; 120:10; 40:12 and 40:13.5. Generally, as the stent frame is axially compressed or elongated, the diameter of the stent frame correspondingly increases or decreases in response and/or subject to external constraints to radial expansion/contraction of the device. Thus, as the length of the stent frame 30 is elongated or contracted the stent frame 30 aspect ratio may accordingly be altered. Alternatively or in addition to, the aspect ratio can be defined at the level of the stent region or ring 40. For example, the aspect ratio of the stent frame 30 can be defined by the ratio of the gap width to gap height of an individual stent ring 40. Elongation of the stent frame 30 will increase the gap length, and due to the interconnection of struts 32, the gap height of the stent ring 40 will respond accordingly thereby altering the aspect ratio of the stent. Alternatively, where the diameter remains constant during elongation, the included angles vary accordingly. For example, the included angles $\alpha$, $\beta$ enlarge due to an elongation of the stent frame 30.

As already noted, the preferred method includes elongating a stent frame 30 to expand the gap length of the gaps 38 in the axial direction to alter the aspect ratio of the stent graft device 10 from an initial unloaded condition to a second aspect ratio. With the stent frame in the elongated state, a tubular graft member is bonded to the stent frame, preferably to the outside of the stent frame 30 or to the inside of the stent frame 30. Preferably, the tubular graft member forms the outer sleeve 20 and is bonded to an inner sleeve 21 of the graft member disposed within the interior of the stent frame 30 so as to encapsulate the stent frame 30 between the inner and outer tubular graft members. Alternatively, the outer and inner sleeves 20, 21 can encapsulate the stent frame using sutures, ultrasonic welding, stapling, and adhesive bonding etc. It is also possible that a single tubular graft member 21 is coupled to the stent graft 30, for instance positioned coaxially inside the stent frame 30. In such a case it is preferable that the tubular graft member 21 is secured to the luminal surface 36. Such an embodiment will be further discussed below with reference to FIG. 7.

Preferably, the outer and inner sleeves 20, 21 are made of ePTFE, but other biocompatible materials are possible including ultra thin wall material (UTW) ranging in thickness from about 0.08 millimeter to about 0.25 millimeter, regular thin wall material (RTW) ranging in thickness from about 0.3 millimeter to about 0.8 millimeter, polyamides, polyimides, silicones, fluoroethylypolypropylene (FEP) polypropylfluorinated amines (PFA), or other fluorinated polymers. The tubular graft members 20,21 when made of ePTFE are made by extruding a PTFE-lubricant mixture through a ram extruder into a tubular shaped extrudate and longitudinally expanding the tubular shaped extrudate to yield a uniaxially oriented fibril microstructure in which substantially all of the fibrils in the ePTFE microstructure are oriented parallel to one another in the axis of longitudinal expansion, as is known in the art and described in U.S. Pat. Nos. 3,953,566; 4,187,390; and 4,482,516 which are expressly incorporated by reference as teaching a method of making longitudinally expanded PTFE extrudates.

The use of unsintered or partially sintered ePTFE tubular extrudates is preferable over fully sintered ePTFE materials, whether in tubular form or in sheet form. The partially sintered ePTFE has a microstructure which is substantially undisturbed during processing and assembly of the stent graft 10 until the final step of fully sintering the ePTFE to encapsulate the stent. The stent encapsulation results in spans of bonded graft material covering the expanded gaps 38 in the stent frame 30. Additionally, or alternatively, the outer graft member 20 or the inner graft 21 is secured to the stent frame 30 on the basis of an intervening polymeric bonding layer, preferably applied to the stent frame 30 prior to coupling the tubular graft member 21 to the stent frame 30. Such an embodiment is further discussed below with reference to FIG. 9.

The method of formation further provides relaxing the assembled stent graft device such that the stent frame is permitted to contract axially. As the stent frame contracts from the elongated state, the encapsulating graft material contracts with the stent frame and the spans of graft material between the gaps 38 or interstices form the expansion folds 22 of the stent graft device 10.

One embodiment of the preferred method of forming the stent device 10 initially provides loading a first tubular graft member 21 about a mandrel and securing the member at both ends. For example, the graft member 21 can be seven millimeter (7 mm.) carbon lined UTW graft or other biocompatible material, and the forming mandrel is preferably a 6.6 millimeter hollow stainless steel mandrel. More preferably, the graft material is a tubular member formed of ePTFE previously as described herein. In a second step, a stent frame 30 is disposed about the first tubular graft material located on the mandrel. Preferably, the stent frame 30 is an 8×50 AV access stent having a flared and non-flared end, or alternatively, the stent frame 30 can be of another configuration such as, for example, any stent frame previously described herein. The non-flared end is preferably secured to the mandrel, and the stent frame 30 is then elongated over the inner or first tubular graft member 21. Preferably, the stent frame 30 is elongated such that the gaps 38 have a gap length of about 0.5 millimeters and the overall stent frame length is about 59 millimeters. Generally, the stent frame 30 is elongated so as to increase the stent frame 30 by about five to about twenty percent, preferably about five to about ten percent, and more preferably about seven percent.

With the stent frame in an elongated state, the flared end can be secured to the mandrel. Preferably, the distance from the end of the mandrel to the end of the flare is determined to define an offset. More preferably, the distance from the end of the mandrel to the end of the flare defines an offset of about 130 millimeters. In a third step, an outer or second tubular graft member is disposed over the elongated stent and secured at both ends thereby forming a graft-stent-graft assembly. Preferably, the second tubular graft member is approximately 7 millimeter graft material. To secure the second tubular graft member, a TEFLON (TFE) tape is preferably applied at each end.

In a fourth step, a wrapping is preferably applied to the length of the assembly. In a preferred wrapping process, the outer tubular graft member 20 is tensioned about the stent frame 30 to form a bond with the interior tubular graft member 21. Preferably, a wrap tension of about 900 gram force (900 gf.) is applied. The bond is formed in the gaps 38 of the stent frame 30. The wrapping can be performed by placing the mandrel, with the stent graft stent assembly disposed about the mandrel in a spiral machine and applying an appropriate tensioning voltage. Alternatively, the wrapping process can be applied by known techniques in the art. Voltage and speed settings can be provided to the spiral machine to effect a desired wrap and bond. Preferably, the wrapping is applied over the length of the assembly at an adequate voltage and at adequate traverse and spindle speeds to effect the desired wrap and bond. The wrapping is preferably stopped to remove the tape securing the non-flared end of the stent. In addition, the wrapping process is preferably applied twice over the length of the assembly, in which the tape removal occurs after the first pass.

Preferably, there is an overlap of the wrap of about 2.0 to 2.5 millimeters, preferably about 2.31 millimeters. With the tape removed from the non-flared end, the remainder of the assembly can be wrapped. In a fifth step, the flared end is released by cutting back a portion of the graft material. Preferably, the graft material is cut back to a location that is about 10 millimeters internal to the measured offset from the loading procedure described above. In a sixth step of the preferred method, the assembly is sintered to bond the first tubular graft member to the second tubular graft member. The assembly can be removed from the mandrel once the assembly has cooled. In a finishing process, the encapsulating graft material can be cut back by laser cutting. A preferred laser cutting machine is, for example, laser cutting machine model number ULS-25PS from UNIVERSAL LASER SYSTEMS, INC. Preferably, the encapsulation material is cut back 10 millimeters internal of the flared end and the 1 millimeter external to the non-flared end. Preferably, the laser cut is performed in spiral machine having an 8 millimeter spiral, at 75% speed, 50% power, 330 ppi with the object height set to 6 inches plus ½ diameter of the cutting mandrel (6.125 inches).

Figure 6:
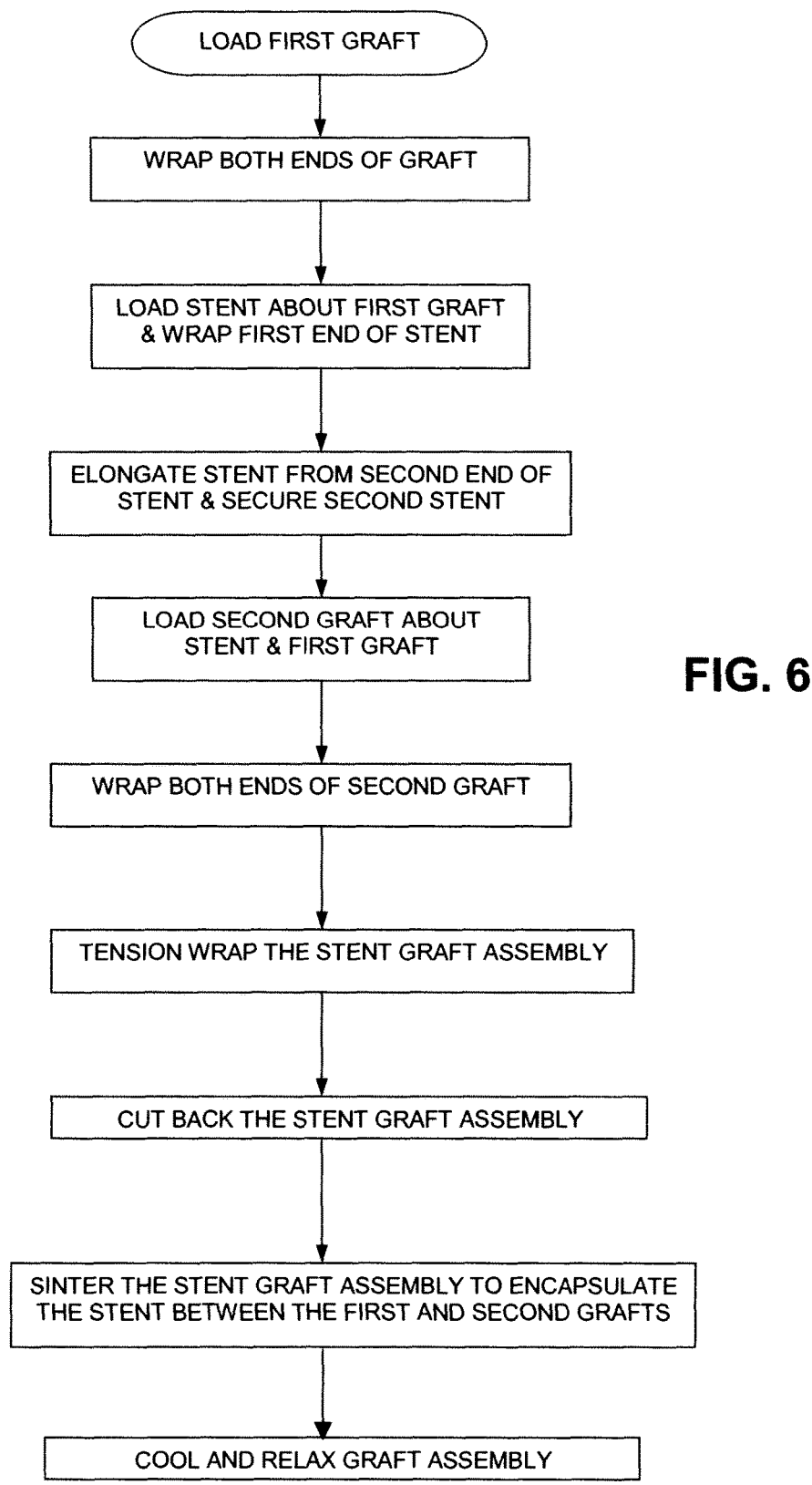
FIG. 6 is an illustrative flow chart of a preferred method for forming a stent graft device.

Shown in FIG. 6 is a illustrative flow chart of this preferred method. In an alternative method, is a tubular graft member 21 coaxially positioned inside the stent frame 30 and, for instance, secured to the luminal surface 36 of the tensioned stent graft 30. The graft member 21 can be secured to the stent frame 30 on the basis of an intervening polymeric bonding layer. Such a layer is applied by powder coating or holding the stent frame 30 in a liquid containing a polymer. The polymer can be PTFE, PET, FEP etc., or any other fluoropolymer. Instead of bonding the inner graft member 21 to outer graft member 20, in this method the inner graft member 21 is during heating, for instance fusing or sintering, bonded to the polymer coating applied to the stent graft 30. Other steps of this alternative method are similar to the steps followed for forming an encapsulated stent graft 30. This embodiment is further discussed below with reference to FIG. 9.

In one aspect of the preferred method, the elongation of the stent frame 30 over the first tubular graft member 21 is made such that the stent frame is elongated to an extreme length. More specifically, the stent frame 30 is elongated from about 50 millimeters to a length of at least about 64 millimeters. In another aspect of the method, the first or inner graft member 21, stent frame 30 and outer graft member 20 are mounted and secured to the mandrel with the stent frame 30 elongated to the extreme length, as previously described. The assembly is then wrapped; stopping long enough to remove the TEFLON tape securing the stent frame. The assembly is then wrapped a second time and then sintered. The assembly is laser cut 10 millimeters from the flared end to release the flare and then the assembly is sintered for an additional period of time. The wrapping process of the method can be further modified to effect the bonding between the inner tubular graft member and the outer tubular graft member. For example, the graft-stent-graft assembly can be disposed and secured about the mandrel and a voltage of 18 volts can be applied. In addition, the assembly can be wrapped three times.

The methods of forming the stent graft device 10 can be further modified by the application of TEFLON tape to the graft-stent-graft assembly prior to sintering in order to control the bond between the inner graft member 21 and outer graft member 22. For example, a band of TEFLON tape can be applied to the circumference of the graft-stent-graft assembly in a manner that avoids the gaps 38 of the stent frame 30. Once the TEFLON tape is secured about the circumference of the assembly, the assembly can be sintered. In another embodiment of the method, the TEFLON tape can be applied to the ends of the assembly. The TEFLON tape can be limited to application at the stent rings 40 at the ends of the assembly, thus leaving the central portion of the assembly unwrapped. The assembly with the TEFLON tape at its ends can be sintered to produce a stent graft device 10 having ends with a smaller diameter than the central portion of the device. In addition, the unwrapped portion of the assembly can leave the inner graft member unbonded to the outer graft member.

In yet another embodiment of the method of forming the stent graft device 10, the outer tubular graft member can be further configured to increase flexibility in the device 10. For example, the outer graft member can be slit in the areas spanning over the gaps 38 in the underlying stent frame 30, and then graft-stent-slitted graft assembly can be wrapped as described, for example, at 10 volts and sintered for 11 minutes. Further in the alternative, the outer graft member can be applied as a plurality of elongated strips radially distributed about the elongated stent frame 30 in a manner as described in U.S. Pat. No. 6,558,414 which is incorporated herein in its entirety.

In an embodiment the stent frame 30 is coated with a polymeric bonding layer 100. Such a polymer coating may be of polytetrafluoroethylene (PTFE), fluorinated ethylene propylene (FEP), polytetrafluoroethylene-perfluoroalkyl vinyl ether copolymer (PFA), polyvinyl chloride (PVC), polypropylene (PP), polyethylene terephthalate (PET), polytuinylidene fluoride (PVDF) and other biocompatible plastics. Methods of applying such a coating 100 to the struts 32 of stent graft 30 are described in WO 98/00090 and include immersing the stent graft 30 in a vessel containing an aqueous dispersion of such a polymer, for instance PTFE. This is also known as dip coating as described in EP 1164972 B1. Numerous ways of spraying techniques may alternatively be employed. It is for instance possible to apply an electrostatic spray process in which a coating powder is withdrawn from a reservoir in an airstream and electrostatically charged in a high voltage corona of a spray gun. This method as well as plasma coating is also described in EP 1164972 B1. The tubular graft member 21 is coaxially positioned inside the stent frame 30 and secured to the stent frame 30 on the basis of the intervening polymeric bonding layer 100. A stent frame 30 with a single graft member 21 bonded to a luminal surface 36 of the stent frame 30 is usually radially contractable to a diameter which is less than the diameter to which a stent graft 30 as encapsulated between an inner graft member 21 and an outer graft member 20.

Figure 7:
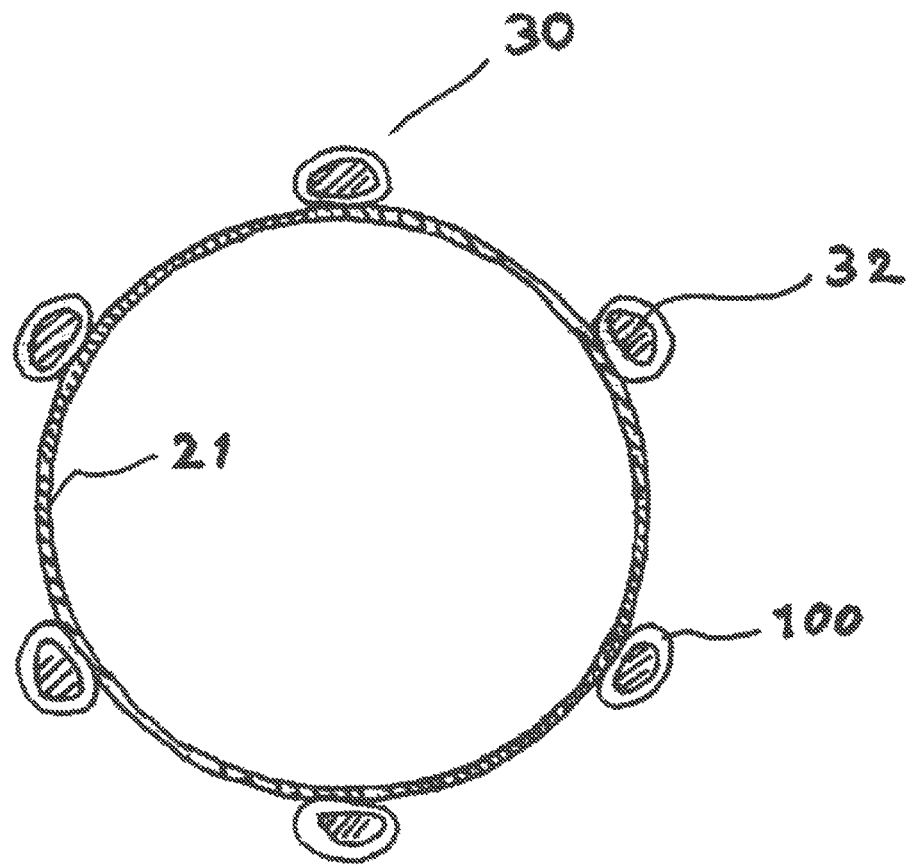
FIG. 7 is a cross sectional view of another preferred stent graft device.
Figure 8A:
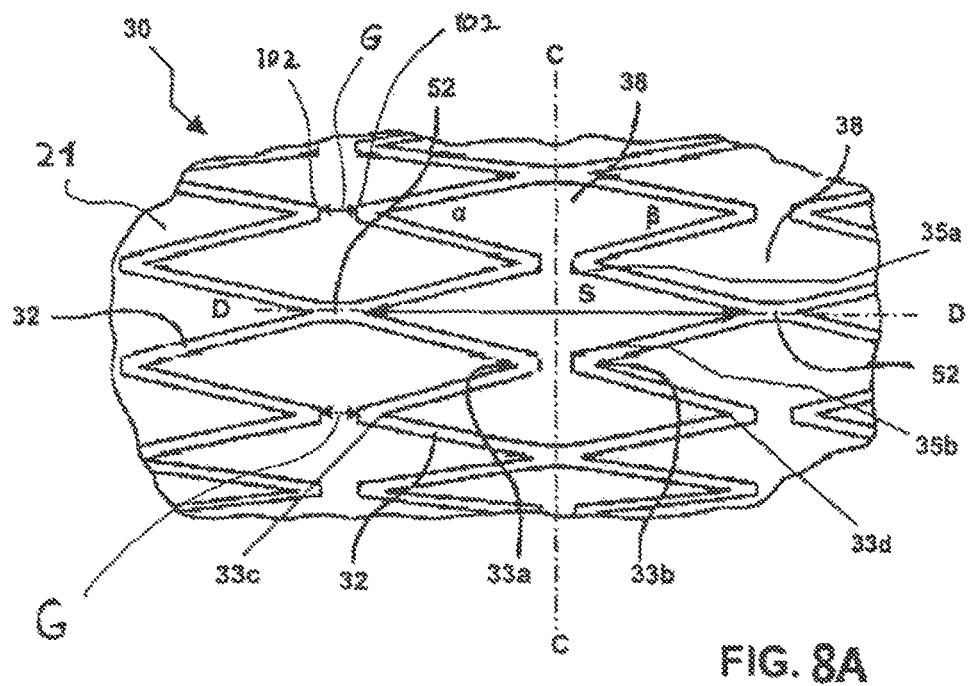
FIG. 8A is a detail of a schematic view of the stent frame in the device of FIG. 7.
Figure 8B:
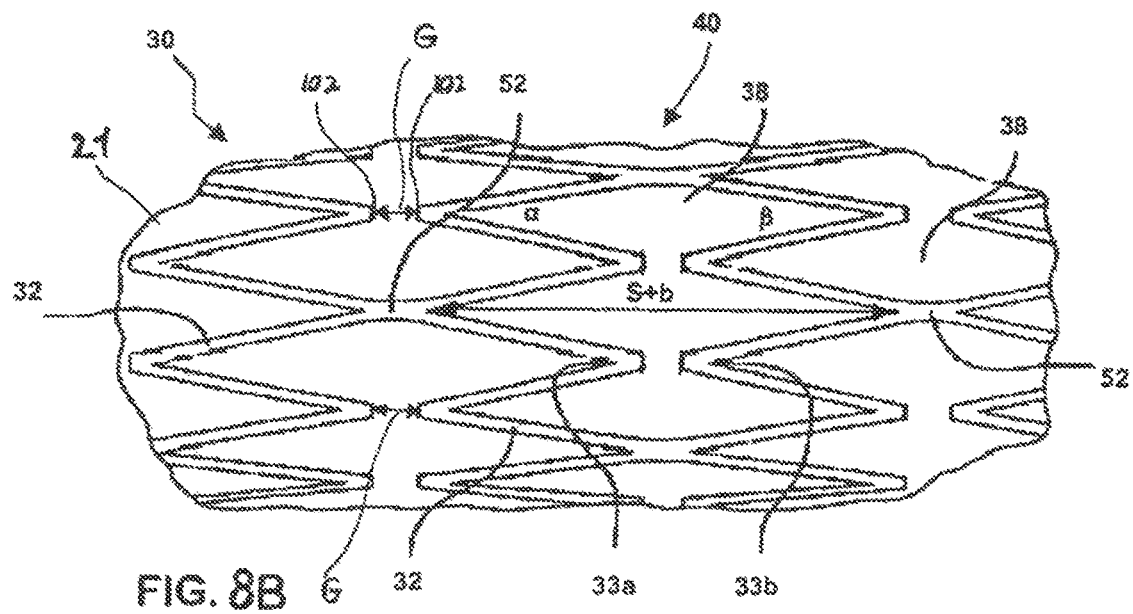
FIG. 8B is another detail of the stent frame in the device of FIG. 7.

With reference to FIG. 8A and FIG. 8B, which show a detail of a schematic view of the stent frame 30 provided with inner graft member 21, of which a cross sectional view is provided in FIG. 7, it is pointed out that a gap G between two opposite apexes 102 can easily be 5% larger in a stretched stent graft assembly according to FIG. 7, as compared to the length of the gap G between the apexes 102 in an unstretched stent graft assembly according to FIG. 7.

Figure 9:
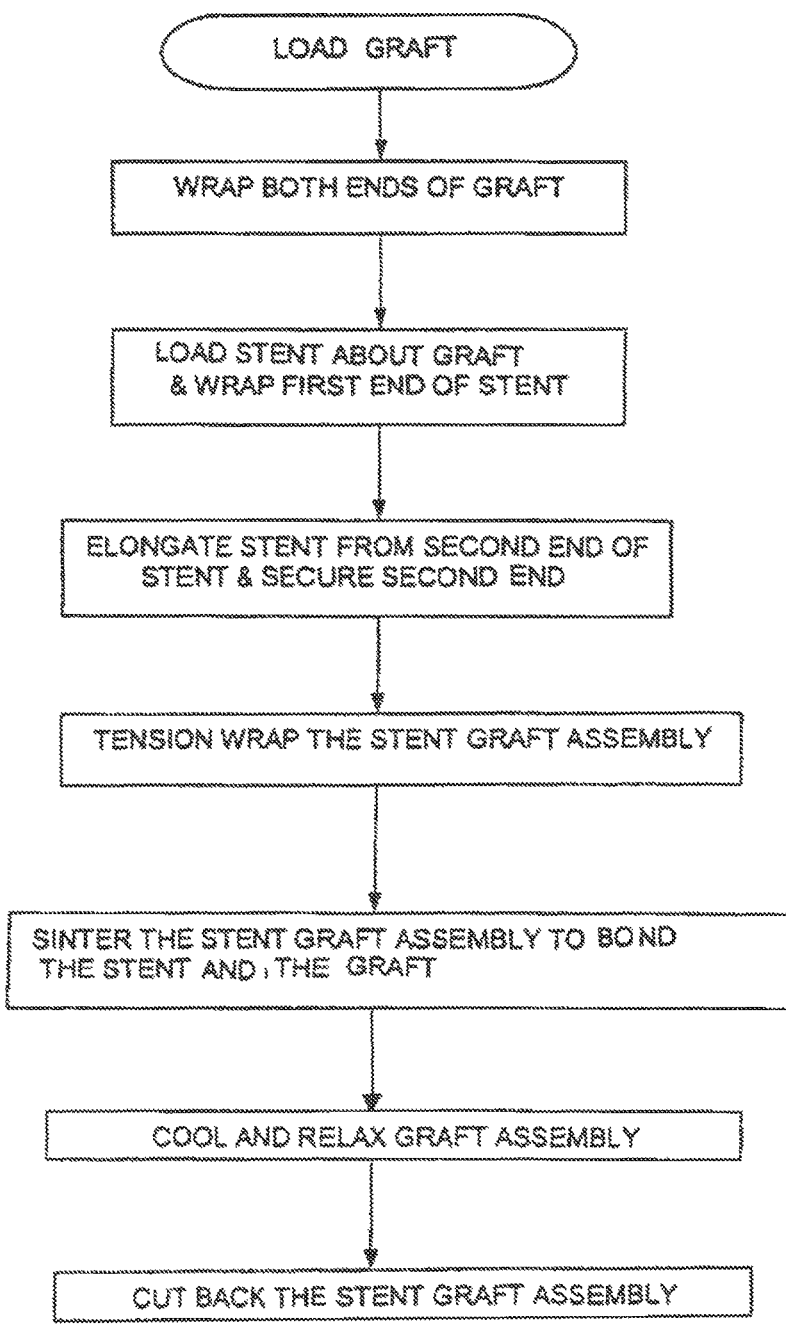
FIG. 9 is an illustrative flow chart of another method for forming a stent graft.

An example of a method for making a stent graft device having graft member 21 coupled the abluminal surface 36 of stent frame 30 is schematically outlined in FIG. 9. A graft member 21 may be dilated and loaded onto a mandrel. Preferably, the graft member comprises tubularly shaped unsintered PTFE. Both ends of the tubular graft layer are secured to the mandrel. A stent graft 30 is disposed about this unsintered PTFE graft member. The stent graft concerns a stent graft which has been coated with a bonding polymer, preferably a fluoropolymer, for instance by methods as discussed above. A first end of the stent is secured to the mandrel, for instance by a well-known wrapping method. The stent is elongated from a second end of the stent and the second end is also secured to the mandrel. The next step concerns wrapping PTFE tape on the outside of the stent for pressing the inside of the stent radially inwards so that the fluoropolymer coating at the inner side of the stent is pressed against the outside of the unsintered PTFE graft layer. The stent graft assembly is then sintered, at a temperature of 370° C. and for a time which is shown to lead to bonding of the stent graft to the stent graft member. A suitable time was found to be about 10 minutes. After, or during, cooling down, the PTFE tape can be unwrapped from the stent graft assembly. The elongated graft assembly can be removed from the mandrel and relax. It is then possible to trim an overhang of the inner graft member 21 to the stent frame 30.

Example One

In a first example of manufacturing a stent graft device 10 according to the preferred method, a first 7 millimeter carbonlined inner UTW graft member was loaded onto a stand, and a 7.7 millimeter solid aluminum loading mandrel was inserted into the graft member to load the graft member on the mandrel. The ends of the first graft member were secured to the mandrel by TFE tape. An 8×50 millimeter stent having a flared end and a non-flared end was loaded onto the outside of the first graft member and centered. The non-flared end was secured to the mandrel by TFE tape and the stent was slightly elongated. The distance from the end of the mandrel to the end of the stent at the flared end was measured. A second 7 millimeter UTW graft member was loaded over the elongated stent, and both ends of the second graft member were secured. The mandrel assembly was placed in a spiral machine and a wrapping process was applied. More specifically, a circumferential pressure or tension was applied to the assembly to cause the first and second graft members to come into contact through the interstices of the stent frame. The wrapping process was stopped at point along the assembly to permit removal of the TFE tape, and the wrapping process was completed along the length of the assembly. The assembly was cut back by laser cutting the assembly at the flared end to release the flare. Preferably, the flared end was cut back at about 10 millimeters. The assembly was then sintered resulting in a flexible stent graft device. Notably, laser cutting the assembly before sintering resulted in an assembly in which 20 millimeters of the original 50 millimeter stent contracted to its original pattern at the flared end, the remainder maintained an elongated configuration.

Example Two

In a second method of manufacturing a stent graft device 10, a 7 millimeter carbon lined inner UTW graft member was loaded onto a 6.6 millimeter hollow stainless steel mandrel and the ends of the first graft member were secured to the mandrel. An 8×50 millimeter stent having a flared and non-flared end was placed on the mandrel and centered. The non-flared end of the stent was taped to the mandrel, and the stent was extremely elongated such that the stent reached a length of about 64 millimeters. The assembly is placed in a spiral wrapping machine and a wrapping process is applied to the length of the device, stopping short to remove the tape from the non-flared end. The wrapping process is continued to completion with the entire assembly being wrapped. The assembly was sintered and laser cut from the flared end, at about 10 millimeters from the flared end of the device, in order to release the flare. The assembly was then additionally sintered. This exemplary method produced a stent graft device that contracted longitudinally, but became rather rigid due to the second sintering cycle.

Example Three

In a third method of manufacturing a stent graft device 10, a 7 millimeter carbon lined inner UTW graft member was loaded onto a 6.6 millimeter hollow stainless steel mandrel and the ends of the first graft member were secured to the mandrel. An 8×50 millimeter stent having a flared and non-flared end was placed on the mandrel and centered. The non-flared end of the stent was taped to the mandrel, and the stent was extremely elongated such that the stent reached a length of about 64 millimeters. The assembly is placed in a spiral wrapping machine and a wrapping process is applied to the length of the device, stopping short to remove the tape from the non-flared end. The wrapping process is continued to completion with the entire assembly being wrapped. The assembly was sintered and laser cut from the flared end at about 10 millimeters from the flared end of the device in order to release the flare.

Example Four

A fourth example of manufacturing a stent graft device 10 substantially similar to the method used in Example One provided, a first 11 millimeter carbon lined inner UTW graft member was loaded onto a stand, and a 10.7 hollow stainless steel mandrel was inserted into the graft member to load the graft member on the mandrel. The ends of the first graft member were secured to the mandrel by TFE tape. An 12×80 millimeter Iliac stent having a flared and a non-flared end was loaded onto the outside of the first graft member and centered. The non-flared end was secured to the mandrel by TFE tape and the stent was slightly elongated and then secured at the flared end. The distance from the end of the mandrel to the to the end of the stent at the flared end was measured then secured at the flared end. A second 11 millimeter UTW graft member was loaded over the elongated stent, and both ends of the second graft member were secured. The mandrel assembly was placed in a spiral machine and a wrapping process was applied. More specifically, a circumferential pressure was applied to the assembly to cause the first and second graft members to come into contact through the interstices of the stent frame. The wrapping process was stopped to permit removal of the TFE tape at the non-flared end, and the wrapping process was completed along the length of the assembly. The assembly was cut after lamination to release the flare at the flared end. Preferably, the flared end was cut back at about 10 millimeters. The assembly was then sintered resulting in a stent graft device exhibiting some flexibility. However, the gaps of the stent frame moved to about 0.5 millimeters apart, and there was limited uniformity in the shape of the gaps of the stent frame.

Example Five

A sample run of six stent graft devices produced by an embodiment of the present method were generated to evaluate the flexibility of the sample devices in addition to the ability of the sample to return to their original length after assembly. Each of the six test samples were produced by providing a first 7 millimeter carbon lined inner UTW graft member loaded onto a stand, and a 6.7 hollow stainless steel mandrel was inserted into the graft member to load the graft member on the mandrel. The ends of the first graft member were secured to the mandrel by TFE tape. An 8×50 millimeter Beta I Memotherm stent having a flared and a non-flared end was loaded onto the outside of the first graft member and centered. The non-flared end was secured to the mandrel by TFE tape and the stent was slightly elongated to a point 130 millimeters from the end of the mandrel. A second 7 millimeter UTW graft member was loaded over the elongated stent, and both ends of the second graft member were secured. The mandrel assembly was placed in a spiral machine and a wrapping process was applied. More specifically, a circumferential pressure was applied to the assembly to cause the first and second graft members to come into contact through the interstices of the stent frame. The wrapping process was stopped at point along the assembly to permit removal of the TFE tape, and the wrapping process was completed again along the length of the assembly. The wrapping process was applied twice to the assembly. The assembly was cut back by laser cutting the assembly at the flared end to release the flare. Preferably, the flared end was cut back at about 10 millimeters, and the assembly was then sintered.

To evaluate impact on elongating the stent frame to the final stent graft device, measurements were taken at three instances during assembly for the sample device. First, an initial length of the stent frame was taken prior to assembly. A second measurement was taken at the elongation of the stent frame; and a final measurement was taken after the assembled device was removed from the mandrel following sintering. Table 1 below shows a range of measured initial, elongated recovered stent lengths for an array of stent graft devices produced by the preferred method.

TABLE 1

| Initial Stent Frame Length (in millimeters) | Elongated Stent Frame Length (in millimeters) | Stent Graft Device Recovered Length (in millimeters) |
| --- | --- | --- |
| 50.4 | 58.95 | 55.1 |
| 50.6 | 57.68 | 54.6 |
| 50.5 | 59.0 | 55.8 |
| 50.7 | 58.69 | n/a |
| 50.6 | 60.5 | 57.0 |
| 50.5 | 58.98 | 55.9 |
| 50.5 | 59.0 | 56.0 |
| 50.5 | 58.85 | 56.0 |

Preferably, the initial stent frame is elongated by about fifteen to about twenty percent (15%-20%) of its initial length. When the stent graft device is removed from the mandrel, the stent frame is relaxed and permitted to recover or contract axially. As indicated by the summary table provided, a stent device 10 can contract to a length that ranges from about one hundred ten percent to about one hundred fifteen percent (110%-115%) of the initial stent frame length, and preferably is about one hundred twelve percent (112%) of the initial stent frame length, depending upon the amount of elongation. Preferably, the stent graft device 10 would recover or rebound from the fully elongated stent frame length to the initial length of the stent frame. However, due to the presence of the graft material, the stent graft device experiences a rebound ranging from about thirty to about fifty percent (30%-50%) of the elongation length which is the length difference between the initial stent length and the fully elongated stent length. Accordingly, the assembled stent graft device 10 includes an expansion length which is the difference between the relaxed and recovered state and the fully elongated state. This expansion length can range from about five percent to about ten percent (5%-10) of the relaxed and recovered length of the stent graft device 10 and is preferably about seven percent (7%) of the relaxed and recovered length of the stent graft device. This expansion length preferably provides the stent graft device 10 with its flexibility and kink resistance.

The expansion length can provide flexibility in the device in at least one aspect by compensating for the foreshortening effect experienced by the stent frame 30 as its inner chamber 18 goes from a collapsed state to a dilated state. For example, an non-elongated stent frame 30 in a collapsed state such as when configured for loading in a stent delivery device, has a gap 38 with a gap length at its maximum. When the stent frame 30 is dilated, for example, about a mandrel, the gap length of gap 38 is reduced. This reduction in gap length can range from about five to ten percent (5%-10%) and is preferably about seven percent (7%). Accordingly, to provide a stent graft device with a flexibility that resists kinking, it is preferred to provide an expansion length of about five to ten percent (5%-10%) and preferably about seven percent (7%) that compensates for any foreshortening experienced when bending the stent graft device 10.

The dimensions of the graft material, stent frame and dilating mandrel can also be altered in any of the methods described herein to produce various embodiments of the stent graft device 10. For example, the dimensions of the graft material, stent frame, and mandrel can be enlarged to produce larger diameter and longer stent grafts. In one embodiment, the stent frame is preferably a 12 millimeter Iliac stent cut to 80 millimeters in length. The stent frame is preferably disposed between two 11 millimeter UTW inner carbon graft members or more preferably between two ePTFE members. The stent frame and graft members are further preferably assembled upon a 10.7 millimeter hollow stainless steel mandrel to produce a longer and larger diameter stent graft device 10. The methods described herein can use a tapered mandrel as described in U.S. Pat. No. 6,214,039 which is incorporated herein in its entirety by reference thereto. Alternatively, other dilating mandrels or devices known in the art that radially expand tubular grafts and stent frames can be used as well.

The mandrel can also be further configured to control the bond between the inner graft member and the outer graft member of the assembly. For example, the mandrel can include a spline to form alternating rings of bonded and unbonded graft material along the length of the stent graft device 10. More specifically in a method of forming the stent graft device 10, the inner graft member and stent frame can be disposed about a mandrel having a spline. The stent frame can be axially elongated on the mandrel such that the gaps 38 of the stent frame 30 are disposed over the splines of the mandrel, and the joints 52 aligned with the splines. Alternatively, the joints can be off-set with respect to the splines of the mandrel. With the stent frame aligned with respect to the splines, the outer graft member can be disposed about the inner graft-stent frame assembly and secured. The graft-stent-graft assembly can be wrapped, for example, at 10 volts and subsequently sintered at 370° C. for 11 minutes.

The method of forming the stent graft 10 can also be further modified by altering the wrapping process including altering the spindle speed and/or the tensioning voltage of the spiral machine used in the process. The spindle speed can range from about fifty to about eighty centimeters per minute and is preferably about seventy centimeters per minute (70 cm/min). The voltage effecting the tension force of the outer tubular graft member 20 about the stent frame 30 in order to bond with the inner tubular graft member 21 can range from about ten to about twenty volts and preferably ranges from about ten to about fifteen volts (10V-15 V). In addition, the sintering process can be modified by altering the sintering temperatures and/or sintering times. The stent graft assembly can be sintered at a temperature ranging from about 350° C. to about 375° c. and is preferably about 370° C. The sintering time can depend upon the sintering temperature, where, for example, the sintering temperature is about 370° C., the sintering time can range from about ten to about fifteen minutes and is preferably about eleven minutes. Generally, the wrapping and sintering processes or steps described herein can be conducted and/or modified in any manner provided they sufficiently encapsulate and bond the outer and inner graft members 20, 21 about the stent frame 30.

The graft material used in either sleeve 21 or outer sleeve 22 can be variably configured so as to include such features as, radiopacity and/or bioresorbablility. For example, bioactive agents can be incorporated with the implantable prosthesis. The agents include (but are not limited to) pharmaceutic agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

As used herein, the singular form of "a," "an," and "the" include the plural referents unless specifically defined as only one. While the present invention has been disclosed with reference to certain preferred embodiments, numerous modifications, alterations, and changes to the described embodiments are possible without departing from the sphere and scope of the present invention, as defined in the appended claims. Moreover, where methods, processes and steps described above indicate that certain events occurring in certain order, those skilled in the art would recognize that the ordering of steps may be modified and that such modifications are within the variations of the described embodiments. Accordingly, it is intended that the present invention not be limited to the described embodiments, but that it have the full scope defined by the language of the following claims, and equivalents thereof.

What is claimed is:

1. A stent device comprising:
 a first ePTFE graft member forming an ePTFE expansion portion;
 a second ePTFE graft member; and
 a stent frame defining a central axis, the frame having an abluminal surface engaged with the first graft member and a luminal surface engaged with the second graft member such that the first graft member and the second graft member together encapsulate the stent frame along the length of the central axis, the stent frame including a configuration where the stent frame is disposed on a curvature such that the abluminal surface has a radius of curvature of approximately 20 millimeters about a center of the curvature and the luminal surface defines a substantially constant effective cross-sectional area at any portion generally transverse to the central axis of the stent frame disposed about the curvature.

2. The stent device according to claim 1, wherein the second graft member is bonded to the first graft member.

3. The stent device according to claim 1, wherein the first graft member defines an outer curved surface and an inner curved surface relative to the center of curvature, the outer curved surface and the inner curved surface being generally equidistant from the central axis.

4. The stent device according to claim 1, wherein the stent frame includes a substantially straight portion continuous with the curvature, the substantially straight portion defining an effective cross-sectional area substantially equal to an effective cross-sectional area proximate the curvature.

5. The stent device according to claim 1, wherein the curvature of the stent frame includes a gap proximate the apex of the curvature, the gap having a gap length, the first graft member expansion portion spanning the gap and defining a radius of curvature substantially equal to about 20 millimeters.

6. The stent device according to claim 1, wherein the radius of curvature ranges from about 30 millimeters to about 10 millimeters.

7. A stent device comprising:
a stent frame having a first end and a second end defining a central axis therebetween; and
a tubular ePTFE graft member extending along the central axis concentrically bound with the stent frame, the ePTFE graft member forming at least one ePTFE undulation between the first and second ends, the undulation spanning a gap in the stent frame in a first substantially straight state of the stent frame such that the undulation extends away from the stent frame, wherein the tubular graft member comprises an inner tubular graft member and an outer tubular graft member which are bonded to each other through openings in the stent frame.

8. The stent device according to claim 7, wherein the stent frame defines a radius of curvature such that the tubular graft member forms an outer curved surface and an inner curved surface, wherein the at least one undulation is located along the inner curved surface.

9. The stent device according to claim 7, wherein the stent frame has a second state wherein the stent frame defines a radius of curvature expanding the gap so as to eliminate the undulation.

10. The stent device according to claim 7, wherein the inner tubular graft member is coaxially positioned inside the stent frame.

11. The stent device according to claim 7, wherein the tubular graft member is secured to the stent frame on the basis of an intervening polymeric bonding layer.

12. The stent device according to claim 11, wherein the polymeric bonding layer comprises a powder coating of, for instance, PTFE or PET applied to the stent frame.

* * * * *